US006969731B1

(12) United States Patent
Tang et al.

(10) Patent No.: US 6,969,731 B1
(45) Date of Patent: Nov. 29, 2005

(54) PROTEASE INHIBITORS THAT OVERCOME DRUG RESISTANCE

(75) Inventors: Jordan J. N. Tang, Edmond, OK (US); Arun K. Ghosh, River Forest, IL (US)

(73) Assignees: The University of Illinois, Board of Trustees, Urbana, IL (US); The Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 09/506,988

(22) Filed: Feb. 18, 2000

Related U.S. Application Data

(60) Provisional application No. 60/120,835, filed on Feb. 19, 1999.

(51) Int. Cl.$^7$ ........................ C07D 307/02; A61K 31/34
(52) U.S. Cl. ........................ 514/473; 514/474; 549/475
(58) Field of Search ................................ 514/473, 474; 549/475

(56) References Cited

U.S. PATENT DOCUMENTS 5,491,149 A * 2/1996 Jadhav ........................ 514/218
5,683,999 A * 11/1997 Jadhav et al. ................ 514/218

FOREIGN PATENT DOCUMENTS

| EP | 0 373 497 A2 | 6/1990 |
| JP | 09143044 | * 6/1997 |
| JP | 09208450 | * 8/1997 |
| WO | WO 92/03472 A1 | 3/1992 |

OTHER PUBLICATIONS

Sugiura, Contact Dermatitis, 1997, 37(2), 90, abstract only, CA 127:210184.*
Carroll, Bioorg Med Chem Lett, vol 8, pp 3203–3206, 1998.*
Carroll, Bioorg Med Chem Lett, vol 8, pp 2315–2320, 1998.*
Baldwin, Structural Biology vol 2(3), Mar. 1995, 244–249.*
Baker & Condon, "Dipeptide isosteres. 1. Synthesis of dihydroxyethylene dipeptide isosteres via diastereoselective additions of alkyllithium reagents to N,N–dimethylhydrazones. Preparations of renin and HIV–1 protease inhibitors transition–state mimics," *J Org Chem* 58:3277–3284 (1993).
Baker, et al., "Nonpeptide renin inhibitors employing a novel 3–Aza (or oxa)–2,4–dialkyl glutaric acid moiety as a P$_2$/P$_3$ amide bond replacement," *J Med Chem* 35:1722–1734 (1992).
Bennett, et al., "The synthesis of novel HIV–protease inhibitors via silica gel assisted addition of amines to epoxides," *SYNLETT* 9:703–704 (1993).
Dreyer, et al., "Inhibition of human immunodeficiency virus 1 protease in vitro: rational design of design of substrate analogue inhibitors," *Proc Natl Acad Sci. USA* 86:9752–9756 (1989).
Marinier, et al., "HIV–1 protease inhibitors: ketomethylene isosteres with unusually high affinity compared with hydroxyethylene isostere analogs," *Bioorganic & Medicinal Chemistry* 2(9):919–925 (1994).

Baldwin, et al., "Structural basis of drug resistance for the V82A mutant of HIV–1 proteinase," *Nat. Struct. Biol.* 2(3):244–9 (1995).
Boger, "Renin Inhibitors. Design of Angiotensinogen Transition–state Analogs Containing Statine:Conformationally restricted inhibitors and a model for the bound conformation of renin substrate," in *Aspartic Proteinases and Their Inhibitors*, (Kostka, V., ed.), pp. 401–420, Walter de Gruyter:N.Y., 1985.
Carpenter, et al., "Antiretroviral therapy for HIV infection in 1998: Updated recommendations of the International AIDS Society–USA Panel," *JAMA* 280(1):78–86 (1998).
Carroll, et al. "Identification of potent inhibitors of *Plasmodium falciparum* plasmepsin II from an encoded statine combinatorial library," *Bioorg. Med. Chem. Lett.* 8(17):2315–20 (1998).
Carroll, et al., "Evaluation of a structure–based statine cyclic diamino amide encoded combinatorial library against plasmepsin II and cathepsin D," *Bioorg. Med. Chem. Lett.* 8(22):3203–6 (1998).
Chen, et al., "Three–dimensional structure of a mutant HIV–1 protease displaying cross–resistance to all protease inhibitors in clinical trials," *J. Biol. Chem.* 270(37):21433–6 (1995).
Coffin, "HIV population dynamics in vivo: implications for genetic variation, pathogenesis, and therapy," *Science* 267(5197):483–9 (1995).
Condra, et al., "Genetic correlates of in vivo viral resistance to indinavir, a human immunodeficiency virus type 1 protease inhibitor," *J. Virol.* 70(12):8270–6 (1996).
Condra, et al., "In vivo emergence of HIV–1 variants resistant to multiple protease inhibitors," *Nature* 374(6522):569–71 (1995).
Craig, et al., "Antiviral properties of Ro 31–8959, an inhibitor of human immunodeficiency virus (HIV) proteinase," *Antiviral Res.* 16(4):295–305 (1991).

(Continued)

*Primary Examiner*—D. Margaret Seaman
(74) *Attorney, Agent, or Firm*—Fulbright & Jaworski, LLP

(57) ABSTRACT

HIV protease inhibitors are among the most powerful drugs in suppressing HIV in human patients. However, HIV developed resistance to all protease inhibitor drugs so far marketed or used in clinical trials. HIV generates resistance by mutating its protease. The strains of HIV containing mutant proteases less vulnerable to inhibitor drug are able to replicate better and maintain the infection. No effective principle exists for the design of resistance-proof HIV protease inhibitors (HIVPr). A new inhibitor has been developed based on a new concept for designing resistance invulnerable HIVPr inhibitors. In vitro data have shown that this inhibitor is effective against many known HIVPr mutants resistant to other HIVPr inhibitor drugs. The new concept is, therefore, generally applicable for the design of other resistance invulnerable HIVPr inhibitor drugs.

2 Claims, 4 Drawing Sheets

OTHER PUBLICATIONS

Debouck & Metcalf, "Human Immunodeficiency Virus Protease: A target for AIDS therapy," *Drug Devel. Res.* 21:1–17 (1990).

Debouck, et al., "Human immunodeficiency virus protease expressed in *Escherichia coli* exhibits autoprocessing an specific maturation of the gag precursor," Proc. Natl. Acad. Sci. USA 84:8903–8907 (1987).

Dorsey, et al., "L–735,524: the design of a potent and orally bioavailable HIV protease inhibitor," *J. Med. Chem.* 37(21):3443–51 (1994).

Dunn, et al., "Subsite preferences of retroviral proteinases," *Methods Enzymol.* 241:254–178 (1994).

Ermolieff, et al., "Kinetic properties of saquinavir–resistant mutants of human immunodeficiency virus type 1 protease and their implications in drug resistance in Vivo," *biochemistry* 36(4):12364–70 (1997).

Ghosh, et al., "3–tetrahydrofuran and pyran urethanes as high–affinity $P_2$ –ligands for HIV–1 protease inhibitors," *J. Med. Chem.* 36:292–94 (1993).

Ghosh, et al., "An efficient synthesis of hydroxyethylene dipeptide isosteres: The core unit of potent HIV–1 protease inhibitors," *J. Org. Chem.* 55:6500–3 (1991).

Graves, "Human immunodeficiency virus Proteinase: now, then, what's next?" *Adv Exp Med Biol.* 306:395–405 (1991).

Gulnik, et al., "Kinetic characterization and cross–resistance patterns of HIV–1 protease mutants selected under drug pressure," *biochemistry* 34(29):9282–7 (1995).

Ho, et al., "Rapid turnover of plasma virions and CD4 lymphocytes in HIV–1 infection," *Nature* 373(6510):123–6 (1995).

Dunn, et al., "Subsite Preferences of Retroviral Proteinases" *Methods in Enzymology* 241:254–278 (1994).

Hong, et al., "Active–site mobility in human immunodeficiency virus, type 1, protease as demonstrated by crystal structure of A28S mutant," *Protein Sci.* 7(2):300–5 (1998).

Hong, et al., "Crystal structures of complexes of a peptidic inhibitor with wild–type and two mutant HIV–1 proteases," *Biochemistry* 35:123–126 (1996).

Hoover, et al., "Discovery of inhibitors of human renin with high oral bioavailability," *Adv Exp Med Biol.* 362:167–80 (1995).

Ido, et al., "Kinetic studies of human immunodeficiency virus type 1 protease and its active–site hydrogen bond mutant A28S," *J. Biol. Chem.* 266(36):24359–66 (1991).

Jacobsen, et al., "Characterization of human immunodeficiency virus type 1 mutants with decreased sensitivity to proteinase inhibitor Ro 31–8959," *Virology* 206(1):527–34 (1995).

Jacobsen, et al., "In vivo resistance to a human immunodeficiency virus type 1 proteinase inhibitor: mutations, kinetics, and frequencies," *J. Infect. Dis.* 173(6):1379–87 (1996).

Kempf, et al., "ABT–538 is a potent inhibitor of human immunodeficiency virus protease and has high oral bioavailability in humans," *Proc. Natl. Acad. Sci. U S A.* 92(7):2484–8 (1995).

Kohl, et al., "Active human immunodeficiency virus protease is required for viral infectivity," *Proc. Natl. Acad. Sci. USA* 85(13):4686–90 (1988).

Lapatto, et al., "X–ray analysis of HIV–1 proteinase at 2.7 A resolution confirms structural homology among retroviral enzymes," *Nature* 342(6247):299–302 (1989).

Lin, et al., "Effect of point mutations on the kinetics and the inhibition of human immunodeficiency type 1 protease: Relationship to drug resistance," *Biochemistry* 34:1143–1152 (1995).

Majer, et al., "Structural based subsite specificity mapping of human cathepsin D using statine–based inhibitors," *Protein Sci.* 6(7):1458–66 (1997).

Marciniszyn, et al., "Mode of inhibition of acid proteases by pepstatin," *J. Biol. Chem.* 251(22):7088–94 (1976).

Mellors, "Closing in on human immunodeficiency virus–1," *Nat. Med.* 2(3):274–5 (1996).

Molla, et al., "Ordered accumulation of mutations in HIV protease confers resistance to ritonavir," *Nat. Med.* 2(7):760–6 (1996).

Mulichak & Watenpaugh, "The crystallographic structure of the protease form human immunodeficiency virus type 2 with two synthetic peptidic transition state analog inhibitors," *J. Biol. Chem.* 268(18):13103–9 (1993).

Navia, et al., "Three–dimensional structure of aspartyl protease from human immunodeficiency virus HIV–1," *Nature* 337(6208):615–20 (1989).

Patick, et al., "Antiviral and resistance studies of AG1343, an orally bioavailable inhibitor of human immunodeficiency virus protease," *Antimicrob. Agents Chemother.* 40(2):292–7 (1996).

Peng, et al., "Role of human immunodeficiency virus type 1–specific protease in core protein maturation and viral infectivity," J. Virol. 63(6):2550–6 (1989).

Poorman, et al., "A cumulative specificity model for proteases from human immunodeficiency virus types 1 and 2, inferred from statistical analysis of an extended substrate data base," *J. Biol. Chem.* 266(22):14554–61 (1991).

Ridky & Leis, "Development of drug resistance to HIV–1 protease inhibitors," *J. Biol. Chem.* 270(50):29621–3 (1995).

Ridky, et al., "Human immunodeficiency virus, type 1 protease substrate specificity is limited by interactions between substrate amino acids bound in adjacent enzyme subsites," *J. Biol. Chem.* 271:4709–4717 (1996).

Rochefort, "Biological and clinical significance of cathepsin D in breast cancer," *Semin. Cancer Biol.* 1(2):153–60 (1990).

Rose, et al., "Human immunodeficiency virus type 1 viral background plays a major role in development of resistance to protease inhibitors," *Proc. Natl. Acad. Sci. USA* 93(4):1648–53 (1996).

Schneider & Kent, "Enzymatic activity of a synthetic 99 residue protein corresponding to the putative HIV–1 protease," *Cell* 54(3):363–8 (1988).

Siman, et al., "Processing of the beta–amyloid precursor. Multiple proteases generate and degrade potentially amyloidogenic fragments," *J. Biol. Chem.* 268(22):16602–9 (1993).

Szelke, "Chemistry of Renin Inhibitors," in, *Aspartic Proteinases and Their Inhibitors*, (Kostka, ed.), pp. 421–441, (Walter de Gruyter:N.Y., 1985).

Tang & Hartsuck, "A kinetic model for comparing proteolytic processing activity and inhibitor resistance potential of mutant HIV–1 protease," *FEBS Lett.* 367(2):112–6 (1985).

Toh, et al., "Is the AIDS virus recombinant?" *Nature* 316(6023):21–2 (1985).

Tomasselli, et al., "The complexities of AIDS: An assessment of the HIV protease as a therapeutic target," *Chimicaoggi–Chemistry Today* 9:6–27 (1991).

Tong, et al., "Crystal structure of human immunodeficiency virus (HIV) type 2 protease in complex with a reduced amide inhibitor and comparison with HIV–1 protease structures," *Proc. Natl. Acad. Sci. USA* 90(18):8387–91 (1993).

Towler, et al., "Functional characterization of the protease of human endogenous retrovirus, K10: can it complement HIV–1 protease?" *Biochemistry* 37(49):17137–44 (1998).

Vacca, "Design of Tight–Binding Human Immunodeficiency Virus Type 1 Protease Inhibitors," *Methods in Enzymology* 241:311–334 (1994).

Wei, et al., "Viral dynamics in human immunodeficiency virus type 1 infection," *Nature* 373(6510):117–22 (1995).

Weiss, et al., *RNA Tumor Viruses*, Cold Spring Harbor:NY, 1984.

Wlodawer & Erickson, "Structure–based inhibitors of HIV–1 protease," *Annu. Rev. Biochem.* 62:543–85 (1993).

Wlodawer, et al., "Conserved folding in retroviral proteases: crystal structure of a synthetic HIV–1 protease," *Science* 245(4918):616–21 (1989).

\* cited by examiner

FIG. 1A U-85548

Saquinavir
(Ro31-8959)

Indinavir
(L-735,524)

Ritonavir
(ABT-538)

UIC-98-056

Molecular Formula: $C_{44}H_{55}N_3O_9S$

Molecular Weight: 801

PROTEASE INHIBITORS THAT OVERCOME DRUG RESISTANCE

This application claims priority to U.S. Ser. No. 60/120,835 filed Feb. 19, 1999 by Jordan J. N. Tang and Arun K. Ghosh.

BACKGROUND OF THE INVENTION

This application is generally in the field of drugs to treat drug resistant pathogens, and in particular relates to protease inhibitors that do not elicit drug-resistant mutations in the pathogens they inhibit, such as the human immunodeficiency virus (HIV).

Drug resistance generally is a problem with the treatment of most pathogens, including bacteria and viruses. A variety of methods have been used, the most common being determining which drugs the pathogen is sensitive to, then treating the patient with a drug that the pathogen is sensitive to. Another approach is the use of a "cocktail", a mixture of two or three different drugs, preferably operating by different mechanisms of action, to block the life cycle of the pathogen before it can develop drug resistance. In the case of a virus such as HIV, this latter approach has been widely adopted, primarily through the use of one or two nucleoside drugs that inhibit replication by interacalation into the viral nucleic acid, in combination with a protease inhibitor that prevents replication. Unfortunately, even with the use of cocktails, HIV mutates extremely rapidly, and becomes resistant even to these combinations of drugs.

The HIV protease gene codes for a protease which, upon-expression as part of the gag-pol protein, procsses gag and gag-pol polyproteins into individual structural proteins and enzymes for the assembly of HIV virions (Debouck et al. (1987), *J. Med. Chem. Res.* 21:1–17). Mutation of the active-site residues of HIVPr renders the mutant virus non-infectious (Kohl et al. (1988), *Proc. Natl. Acad. Sci. USA* 85:4686–4690; Peng et al. (1989), *J. Virol.* 63:2550–2555), which established the HIVPr as a therapeutic target. As a result, many HIVPr inhibitors have been synthesized and tested (Wlodawer and Erickson (1993), *Ann. Rev. Biochem.* 62:843–855), among which four have been marketed: saquinavir (Ro 31–8959, Craig et al. (1991), *Antiviral Res.* 16:295–305), indinavir (L-735,524, Dorsey et al. (1994), *J. Med. Chem.* 37:3443–3451), ritonavir (ABT-538, Kempf et al. (1995), *Proc. Natl. Acad. Sci. USA* 92:2484–2488) and nelfinevir (Patick et al. (1996), *Antimicrob. Agents Chemother.* 40:292–297). Structures are shown in FIGS. 1a–d. These drugs are among the most powerful compounds to suppress HIV replication, as demonstrated both in tissue culture and in clinical trials (Wei et al. (1995), *Nature* 373:117–122; Ho et al. (1995), *Nature* 373:123–126). Combination therapies including HIVPr inhibitors have offered the best results so far to control AIDS (Mellors, (1996), *Nat. Med.* 2:274–276).

Rapid progress on the structure and activity of HIVPr has taken place since the discovery that it is an aspartic protease (Toh et al. (1985), *Nature* 315:691–692). These include the identification of the HIVPr genome, expression and purification of recombinant enzyme, total chemical synthesis (Schneider and Kent (1988), *Cell* 54:363–368), crystal structure of HIV-1 protease (Wlodawer et al. (1989), *Science* 245:616–621; Navia et al. (1989), *Nature* 337:615–620; Lapatto et al. (1989), *Nature* 342:299–302) and HIV-2 protease (Mulichak and Watenpaugh (1993), *J. Biol. Chem.* 268:13103–13109); Tong et al. (1993), *Proc. Natl. Acad. Sci. USA* 90:8387–8391; Chen and Kuo (1994), *J. Biol. Chem.* 270:21433–21436) and many enzymic property and inhibition studies. These results are well documented in reviews (Debouck and Metcalf (1990), *Drug Devel. Res.* 21:1–17; Tomaselli et al. (1991), *Chimicaoggi-Chemistry Today* 9:6–27; Graves (1991), *Adv. Exp. Med. Biol.* 306:395–405; Wlodawer and Erickson (1993), *Science* 245:616–621); and a book (Kuo (1994), *Methods in Enzymology* Vol. 241).

The active HIVPr is a homodimer of 99-residue monomers. The active-site cleft is located between two monomers with two $Asp^{25}$ residues forming the catalytic apparatus. The active-site cleft is covered by two flaps and can accommodate eight substrate residues. The specificity of the enzyme is somewhat broad (Poorman et al. (1991), *J. Biol. Chem.* 266:14554–14561) which is consistent with the sequence differences of the eight natural processing sites. An unique specificity of HIVPr is the ability to cleave an X-Pro bond, which appears to be related to the mobility of the active site of the enzyme (Hong et al. (1998), *Protein Sci.* 7:300–305). The specificity of the subsite pockets is also influenced by the side chains bound in adjacent pockets (Ridky et al. (1996), *J. Biol. Chem.* 271:4709–4717).

Each of the four commercial HIVPr inhibitor contains an isostere —CH(OH)—CH$_2$— which mimics the transition state in the catalytic mechanism of aspartic proteases (Marciniszyn et al., 1976), *J. Biol. Chem.* 251:7088–7094) thereby rendering the tight binding properties of the inhibitor. The position of the isostere, which is equivalent to that of the scissiled bond in the substrate, defines the subsite binding for the inhibitor residues. An example can be seen in a non-commercial inhibitor U-85548 in FIG. 1a. The commercial inhibitor drugs, which require good pharmacokinetic properties and high potency, are typically shorter and have less well defined residue boundaries (FIGS. 1b–d). The interaction of subsite residues in HIVPr with the inhibitors are generally known from the crystal structures of the HIVPr-inhibitor complexes (Wlodawer and Erickson, 1993). The ability of HIVPr inhibitors to suppress HIV replication has been demonstrated in tissue culture and in clinical trials (Wei et al., 1995; Ho et al., 1995). The use of HIVPr inhibitors along with other drugs in combination therapy has offered the best results so far in suppressing HIV propagation in vivo (Mellors, 1996).

The first transition-state analogue of aspartic proteases discovered was pepstatin by Marciniszyn et al. (1976). In this study, the hydroxyethylene group, —CH(OH)—CH$_2$—, was identified to mimic the transition state of catalysis with two carbons in tetrahedral conformation, as contrast to the planar conformation of the peptide bond in the substrate. It was concluded that the potency of pepstatin inhibition was related to the presence of this transition-state mimicry in this (isostere) structure. Because the aspartic proteases share common active-site structure and catalytic mechanism, the transition-state isosteres are applicable to all enzymes of this family. This principle was used later to design inhibitors for renin (Szelke, 1985; Boger, 1985) and HIVPr inhibitors (Tomaselli et al., 1991). Other types of isosteres were later designed and shown to be effective in aspartic protease inhibitors. These include, in addition to hydroxyethylene, dihydroxyethylene [—CH(OH)—CH(OH)—], hydroxyethylamine [—CH(OH)—CH$_2$—NH—], phosphinate [—PO(OH)—CH$_2$—] and reduced amide [—CH$_2$—NH—] (Reviewed by Vacca, 1994). In all cases, including the commercial HIVPr inhibitor drugs, a single transition-state isostere is used in an inhibitor since it minics a substrate peptide with a single hydrolysis site.

The development of resistance to HIVPr inhibitors by the mutation of the HIVPr gene has been clearly demonstrated in in vitro experiments (reviews: Mellors et al. (1994), *Nat. Med.* 2:760–765; Ridky and Leis (1995), *J. Biol. Chem.* 271:4709–4717) and in clinical trials (Wei et al. (1995), *Nature* 373:117–122; Ho et al. (1995), Nature 373:123–126; Jacobsen et al. (1996), *J. Infect. Diseases* 173:1279–1389; Condra et al. (1996), *J. Viol.* 70:8270–8276; Molla et al. (1996) *Nat. Med.* 2:760–765). The in vitro selection of resistant mutants typically takes many passages of HIV in cell culture with increasing inhibitor concentrations for each passage. In patients, the resistance occurs within weeks, owing to the fast replication of virus and fast turnover of the CD4+ T-cells (Coffin, (1995), *Science* 267:483–489).

Comment: U-85548 is an HIV protease inhibitor, but it is not marketed as anti-HIV drug. We use U-85548 here to illustrate the principle of HIV Protease inhibitor design. The other 3 (1*b*, 1*c*, 1*d*) are drugs.

SUMMARY OF THE INVENTION

Protease inhibitors, especially viral protease inhibitors such as HIVPr inhibitors, which are effective against drug resistance resulting from the mutations in the protease gene have been developed. These compounds contain two or more isosteres —CH(OH)—CH$_2$— which mimic the transition state in the catalytic mechanism of the protease. Design and testing of the inhibitors containing two or more isosteres is demonstrated using an HIVPr inhibitor. Unlike known commercial HIVPr inhibitors, these inhibitors do not contain only one isoster having a single orientation which binds to the HIVPr active site at only one mode. These HIVPr inhibitors bind to HIVPr in two or more modes. They not only bind to the protease active site more tightly, but exhibit significantly better activity against HIVPr-resistant mutants and are less prone to development of resistance.

BRIEF DESCRIPTION OF THE DRAWINGS

FIGS. 1*a*–1*d* are formulas of U-85548 (FIG. 1*a*) and known HIVPr inhibitors which have been clinically marketed; Saguinavir™ or Ro31-8959 (FIG. 1*b*); Indinavir or L-735,524 (FIG. 1*c*); and Ritonavir™ ABT-538 (FIG. 1*d*).

DETAILED DESCRIPTION OF THE INVENTION

Figure 1B:
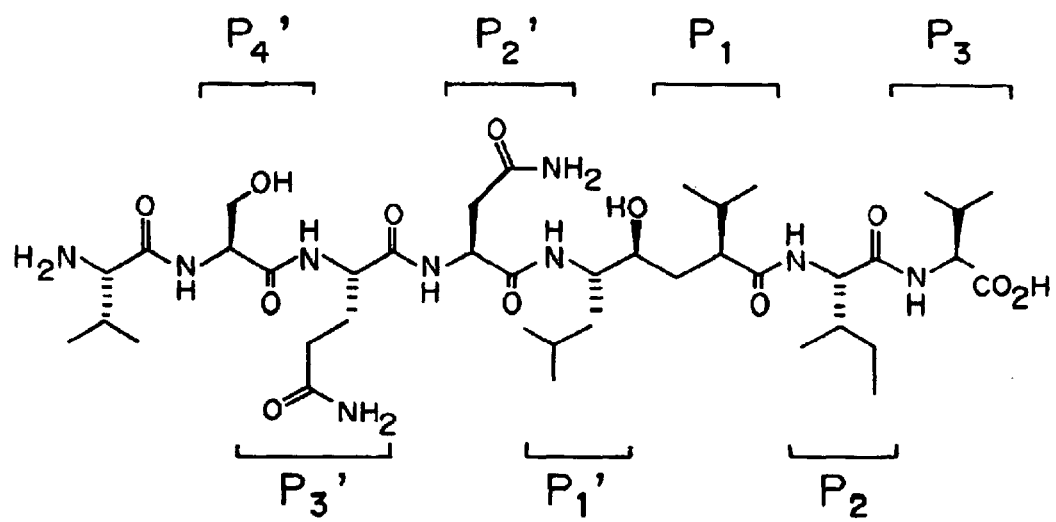
Figure 1B:
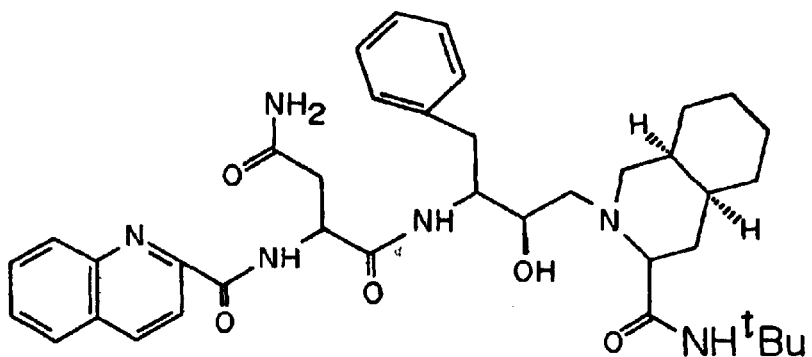
Figure 1C:
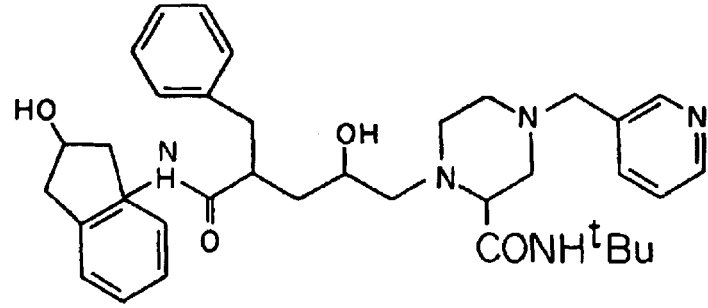
Figure 1D:
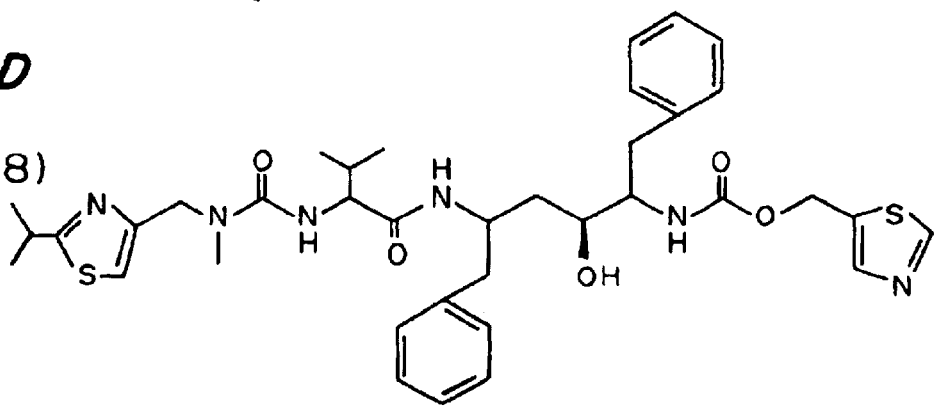

The design and testing of these protease inhibitors is exemplified using HIVPr inhibitors. It is understood, however, that this concept is generally applicable to protease inhibitors, especially aspartic acid protease inhibitors.

Design of HIVPr Inhibitors Effective Against Drug Resistant Mutants

The large body of data on HIVPr resistant mutants selected in the presence of inhibitors in vitro and in vivo can be summarized as follow:

(a) The resistant mutants observed in vitro and in vivo appear in both systems at high frequencies.

(b) Many mutations unrelated to resistance are observed in both systems. Additional tests using enzyme inhibition and inhibitor tolerance by HIV mutants are able to clearly establish the resistant mutants.

(c) Resistant mutations differ with inhibitors (Rose et al. (1996), *Proc. Natl. Acad. Sci.,* 93:1648–1653).

(d) Mutants selected from a patient with resistance often, but not always, cross resist to other inhibitors (Gulnik et al. (1995), *Biochemistry,* 34:9282–9287; Rose et al. (1996), *Proc. Natl. Acad. Sci. USA* 93:1648–1653; Condra et al. (1996), *J. Viol.,* 70:8270–8276; Molla et al. (1996), Nat. Med. 2:760–765).

(e) In vivo selections produced a consistent and ordered pattern of time-dependent increase of mutation sites per protease molecule (Condra et al. (1995), *Nature* 374:469–471; Jacobsen et al. (1996), *Virology* 206–527–534; Condra et al. (1996), *J. Viol.* 70:8270–8276; Molla et al. (1996), *Nat. Med.* 2:760–765. Increased number of mutation sites correlates with less sensitivity to inhibitors. These studies clearly demonstrated that mutation of HIVPr is responsible for the resistance.

Emerging from clinical resistance studies is a group of about 15 mutation sites on HIVPr (Table I) which account for the resistance of the protease inhibitor drugs, saquinavir, indinavir and ritonavir, and cross resistance of many other inhibitors Rose et al. (1996), *Proc. Natl. Acad. Sci. USA* 93:1648–1653.

TABLE I

HIV-1 protease resistant mutants compiled from the result of clinical trials against three commercial HIVPr inhibitor drugs indinavir, ritonavir and saquinavir.

| Position | 10 | 15 | 20 | 24 | 36 | 46 | 48 | 54 | 63 | 64 | 71 | 82 | 84 | 90 | 93 |
|---|---|---|---|---|---|---|---|---|---|---|---|---|---|---|---|
| Wild Type | L | I | K | L | M | M | G | I | L | I | A | V | I | L | I |
| Indinavir | I | | M | I | | I | | V | P | V | V | A | V | M | |
| | V | | R | | | L | | | A | | T | F | | | |
| | R | | | | | | | | | | | T | | | |
| Ritonavir | I | V | R | | | I | I | | V | P | | V | F | V | L |
| | | | | | | | | | | | | A | | | |
| Saquinavir | I | | | | | I | | V | V | P | | | I | V | M |
| | V | | | | | | | | A | | | | | | |

Residues are indicated by single-letter amino acid codes, where A=Ala, F=Phe, G=Gly, I=Ile, K=Lys, L=Leu, M=Met, P=Pro, R=Arg, T=Thr and V=Val In Vitro Demonstration of Resistance to Inhibition by HIVPr Mutants.

It is now well accepted that for an HIVPr mutant to prosper in the presence of an inhibitor drug, the mutant enzyme must retain sufficient catalytic activity, which can be expressed in $k_{cat}/K_m$, with reduced sensitivity to the inhibitor (with increased $K_i$) (Ermolieff et al., 1997), *Biochemistry* 36:12364–12370). The most complete kinetic model developed to determine the activity of HIVPr (wild type or mutants) was described by Tang and Hartsuck (1995), *FEBS. Lett.* 367:112–116). In this model, the processing activity of wild-type and mutants HIVPr, α, at a given inhibitor concentration, [I], is calculated from kinetic parameters $k_{cat}$, $K_m$ and $K_i$ based on the equation $$\alpha = \sigma\{(k_{cat}/K_m)/[1+([I]/K_i)]\}$$

where σ is a constant. This model has been shown to agree with the clinical resistance data. Since the values of $k_{cat}/K_m$ are almost always lower in resistant mutants than in the wild-type HIVPr, it is not suited as a criteria for in vitro evaluation of resistance. On the other hand, the $K_i$ values of different known resistant mutants have good correlation to clinical resistance and can be used to indicate if resistance is taking place against an inhibitor.

Structural Changes from the Wild-type to Resistant HIVPr's.

The resistant mutants of HIVPr inhibitors have three dimensional structural changes from that of the wild-type enzyme. The x-ray crystal structures of several resistant mutants of HIVPr have been studied (Chen et al., 1995, *J. Biol. Chem.* 270:21433–21436; Baldwin et al., 1995, *Nature Struct. Biol.* 2:244–249; Kervinen et al., 1996, *Protein & Peptide Lett.* 6:399–406; Hong et al., 1996 & 1997, Biochemistry 35:123–126, *Structure and Function of Aspartic Proteases: Retroviral and Cellular Enzymes* (M. N. G. James, ed.). The structural basis underlying the mutation/resistance have also been analyzed by comparing the structures of wild-type and mutant HIVPr complexed to the same inhibitors. Although not all the structural factors involved in resistance is understood at the present, it is known that one of the most frequent structural changes as a consequences of resistant mutation of HIVPr is the change of the subsite side chain pockets of the enzyme which causes the inhibitor to bind less effectively. Some of the resistant mutation sites are not located in the subsite pockets. However, due to the flexibility of HIVPr conformation (Ridky et al., 1996), *J. Biol. Chem.* 271:4709–4717), the change of subsite pocket conformation can be induced from a distance.

Design and Test of HIVPr Inhibitors that are Less Vulnerable to Resistance

Design Principles of Current Inhibitors which are Vulnerable to Resistance

To date, all HIVPr inhibitors tested produced HIV resistance in clinical trials because of viral mutations and selection. The main reason for such uniformity is that these inhibitor drugs are designed by the same principle as follows:

In all these inhibitors, an isostere is placed in the polypeptide backbone (or equivalent) of the inhibitor to mark the position of the scissile peptide bond and to mimic the transition state. As illustrated in two examples below, the position of the isostere (as shown by *) defines the assignments of the side chains (A to F) to different subsites of the enzyme. (There are eight subsites). By convention, the substrate subsites on the amino-terminal side of the scissile bond are $P_1$, $P_2$, $P_3$ and $P_4$ in that order, and the substrate subsites on the carboxyl-terminal side of the scissile bond are $P_1'$, $P_2'$, $P_3'$ and $P_4'$. The 8 corresponding subsite binding pockets in the enzyme are named $S_1$ (for binding $P_1$), $S_2$ (for binding $P_2$) . . . and so on.

| Inhibitor 1: | | | | | | | | |
|---|---|---|---|---|---|---|---|---|
| Sequence | A | B | * | C | D | | E | F |
| Subsites | $P_2$ | $P_1$ | | $P_1'$ | $P_2'$ | | $P_3'$ | $P_4'$ |
| Inhibitor 2: | | | | | | | | |
| Sequence | A | B | | C | D | * | E | F |
| Subsites | $P_4$ | $P_3$ | | $P_2$ | $P_1$ | | $P_1'$ | $P_2'$ |

Even though the residues (A–F) and their sequences in these two inhibitors are the same, the individual residues (A to F) bind different subsites of the enzyme for two inhibitors because the position of the isostere is different.

The side chains of the inhibitor are designed to fill the subsite pockets of HIVPr, thus creating a tight binding.

It is clear from the in vitro and clinical studies that HIV-1 mutation/resistance can defeat any structure generated by this principle.

Design Principle for HIVPr Inhibitors that can Withstand Mutation-resistance.

A new principle for the design of HIVPr inhibitors less vulnerable to mutation-resistance has been developed. The principle is based on placing two isosteres in a single inhibitor. In such an inhibitor, as illustrated in the example, inhibitor 3, below, each residue (A to F) has two subsite-assignments:

| Inhibitor 3: | | | | | | | | | |
|---|---|---|---|---|---|---|---|---|---|
| Sequence | A | B | * | C | D | * | E | F | |
| Subsites | $P_2$ | $P_1$ | | $P_1'$ | $P_2'$ | | $P_3'$ | $P_4'$ | using left isostere |
| Subsites | $P_4$ | $P_3$ | | $P_2$ | $P_1$ | | $P_1'$ | $P_2'$ | using right isostere |

For example, depending upon which of the two isosteres is used to bind HIVPr, the residue A can be in either $P_2$ or $P_4$ and residue E can bind in either $P_3'$ or $P_1'$ and so on.

The theoretical ability of a two-isostere inhibitor to fight against mutation-resistance of HIV is illustrated in the following example. A resistant mutation of HIVPr in subsite binding pocket $S_2$ against inhibitor 2 (as described above) would need only to reduce the affinity against residue C. In inhibitor 3, however, the same mutation would need to reduce the affinity of both residues A and C. This is a much more difficult task, especially when residues A and D are structurally different. Even if resistance to 2 residues can be done by multiple mutations in the same subsite, the resulting mutant HIVPr will likely have much less catalytic activity (Ermolieff et al., 1997), thus rendering the mutant strain HIV ineffective.

There is also a kinetic benefit for the two-isostere inhibitors over the one-isostere inhibitors. The two binding modes of a two-isostere inhibitor to HIV protease are represented by the following two equations:

$$E_{free} + I_{free} = EI_1 \tag{1}$$

$$E_{free} + I_{free} = EI_2 \tag{2}$$

where $E_{free}$ and $I_{free}$ are unbound enzyme and inhibitor respectively. $EI_1$ and $EI_2$ are inhibitor bound to enzyme by a first isotere and by the second isotere, respectively. The dissociation constants, or inhibition constants, of the equations (1) and (2) and $K_{i,1}$ and $K_{i,2}$ respectively. The overall inhibition constant, $K_i$, of a two-isostere inhibitor for the enzyme is $$K_i=(K_{i,1} \times K_{i,2})/(K_{i,1}+K_{i,2}) \quad (3)$$

The kinetic benefit of a two-isostere inhibitor can be seen in following examples.

(a) Assuming $K_{i,1}$ and $K_{i,2}$ both to be $1 \times 10^{-9}$M, based on equation (3), the overall inhibition constant, $K_i$, is $0.5 \times 10^{-9}$M, lower than either $K_{i,1}$ or $K_{i,2}$.

(b) Assuming $K_{i,1}$ and $K_{i,2}$ both to be $1 \times 10^{-9}$M and $K_i$ to be $0.5 \times 10^{-9}$ M for the wild-type HIV protease, and assuming Ki,2 increases 10-fold to $1 \times 10^{-8}$ M against a resistant mutant of HIV protease, the overall inhibition constant, $K_i$, for the resistant mutant is $0.9 \times 10^{-9}$ M, a less than two-fold increase over that of the wild-type enzyme.

Thus, the kinetic benefit based on equation (3) will not only lower the $K_i$ of the inhibitor, but also resist the $K_i$ increase (decrease binding intensity) by resistant mutations.

Applicability to Development of Other Inhibitors

Although described herein with specific reference to design of HIVPr inhibitors, it is readily apparent that this concept is generally applicable to the development of effective therapeutics which are targeted against other proteases, especially those aspartic proteases of viral origin.

For example, human cathespin D is involved in breast cancer metastasis (Rochefort (1990) *Semin. Cancer Biol.* 1: 153–160) and in the development of Alzheimer disease in the brain (Siman et al. (1993) *J. Biol. Chem.* 268: 16602–16609). The design of transition-state inhibitors for cathespin D to control these diseases has been attempted (Majer et al. (1997) *Protein Sci.* 6: 1458–1466). Human renin, an aspartic protease, is the target for inhibitor design of isostere-containing transition-state inhibitors for the control of hypertension (Hoover et al. (1995) *Adv. Exptl. Med. Biol.* 362: 167–180. There are a number of examples of proteases in pathogens. For example, malaria causing protozoa *Plasmodium* contains two aspartic proteases, plasmepsin I and II, which are also targets for transition-state inhibitor drugs (Carroll et al. (1998) *Bioorg. Med. Chem.* 8: 2315–2320; Carroll et al. (1998) Bioorg. Med. Lett. 8: 3203–3206). Retroviruses, which cause in addition to immunodeficiency and leukemia in human and animals and different tumors, contain aspartic proteases with processing functions similar to that of HIV protease (Weiss et al. (1984) *RNA Tumor Viruses, Molecular biology of Tumor Viruses*, Second Edition, Vol. 1, Cold Spring Harbor, N.Y.). These proteases are all drug design targets for the control of diseases. The human genome also contains an endogenous virus which expresses active aspartic protease, which has been studied for inhibition by transition-state, isostere-containing inhibitors (Towler et al. (1998) *Biochemistry* 37: 17137–17144). Drugs targeted to these protease can benefit from the design utilizing two or more isosteres in a single inhibitor molecule in order to enhance the potency and withstand development of resistance. Examples of other isosteres which mimic the transistion state of aspartic protease catalysis are shown by Vacca, "Design of Tight-Binding Human Immunodeficiency Virus Type 1 Protease Inhibitors", Methods in Enzymology, 241, 313–333(1994).

Pharmaceutical Compositions

The protease inhibitors described herein are administered to a patient in need of treatment, or prophylactically, using methods and formulations similar to those for other HIVPr inhibitors. The protease inhibitor is preferably administered orally. In the case of HIVPr inhibitors, the protease inhibitor is most preferably administered as part of a "cocktail" including other anti-HIV compounds such as the nucleosides like AZT. The most recent guideline for such therapy by the International AIDS Society is described in Carpenter, Fischel, Hammer et al. (1998) *J. Am. Med. Assoc.* 280: 78–86. The regimens and the choice of drug combinations are dependent on the resistance genotype and phenotype of the HIV strains. The therapeutic strategy is summarized by Larder, Richman and Vella (1998) HIV Resistance and Implications for Therapy, MediCom.

This process is demonstrated by the following non-limiting example.

EXAMPLE 1

Design and Synthesis of Two-isostere HIVPr Inhibitor UIC-98-056

Figure 2:
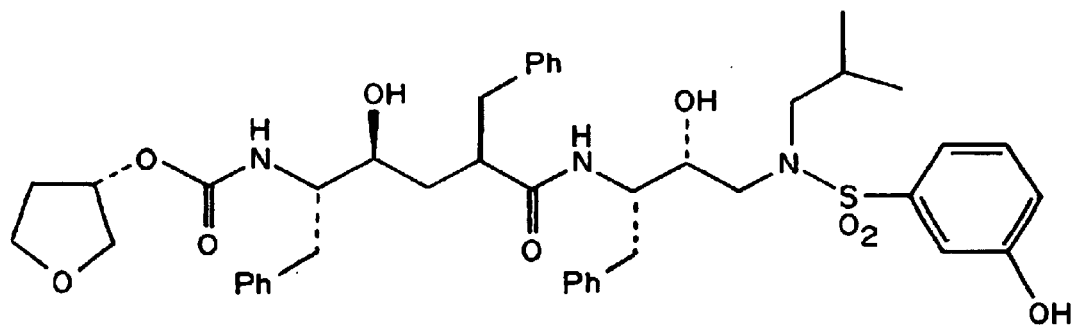
FIG. 2 is a schematic of UIC 98-056.

Based on the principle described above and other considerations, HIVPr inhibitor UIC-98-056 was designed and synthesized. The structure of this inhibitor is shown in FIG. 2.

Synthesis of HIV Protease Inhibitor UIC-98-056

Figure 3:
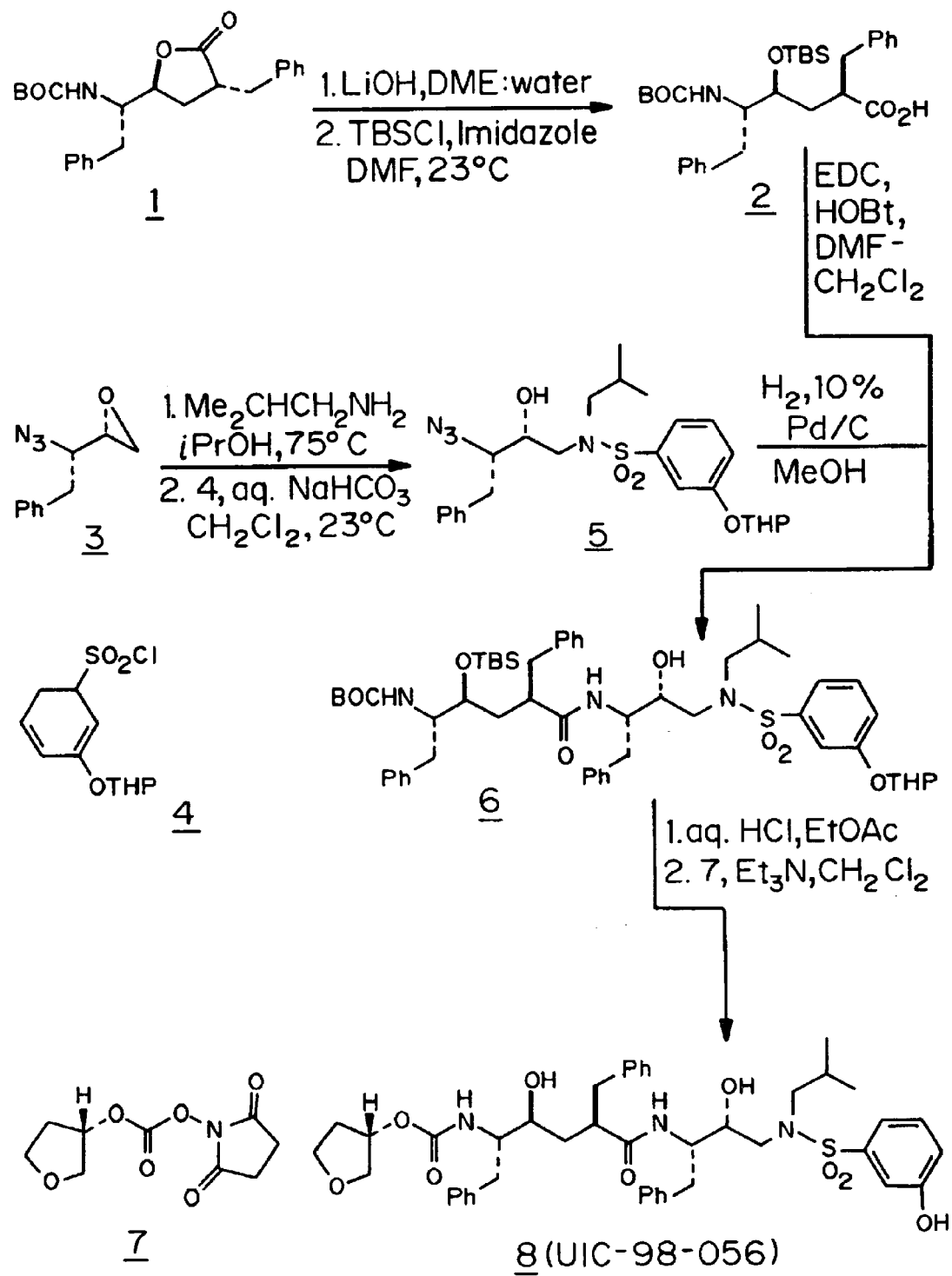
FIG. 3 is a schematic of the synthesis of UIC-98-056.
Figure 4:
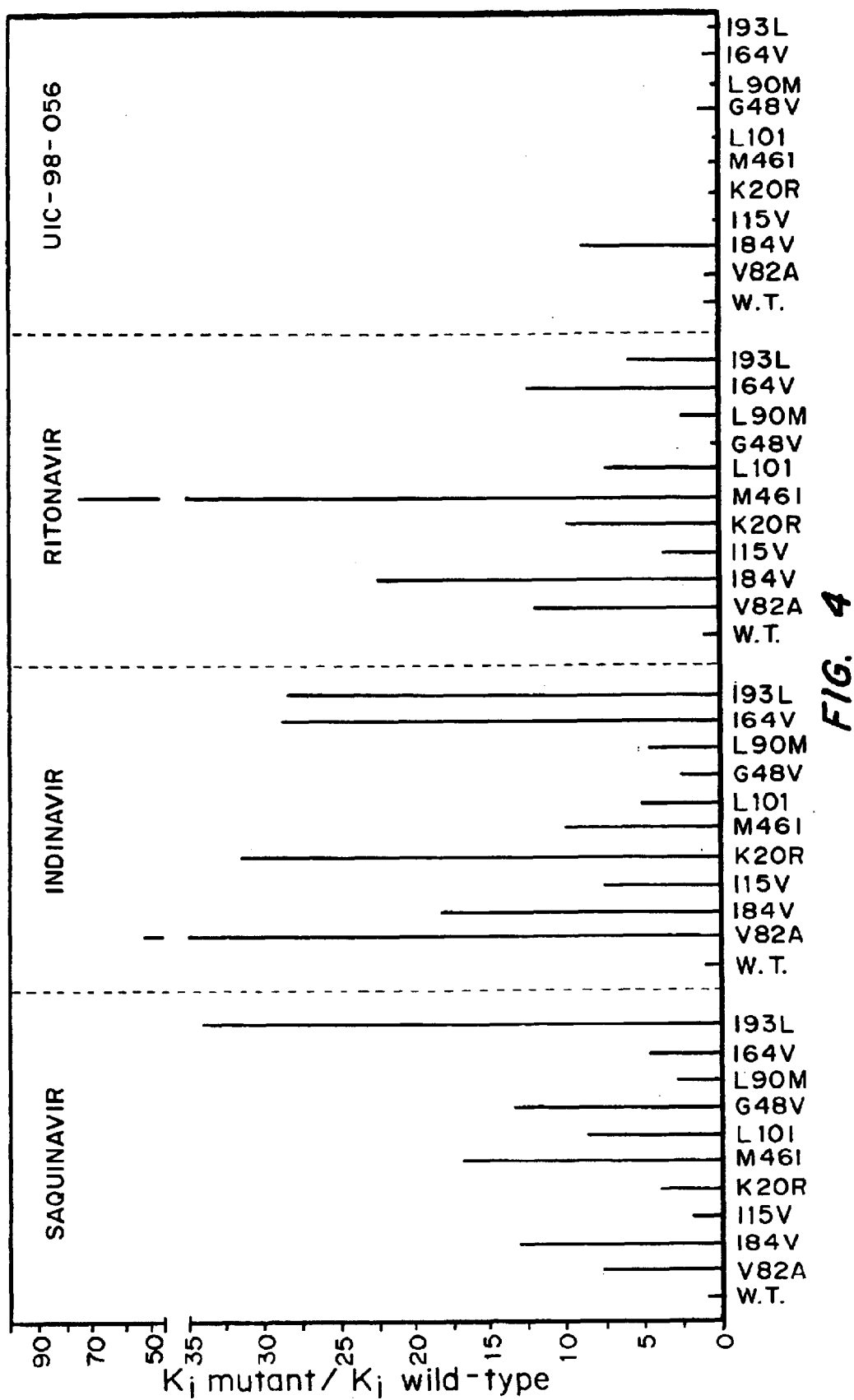
FIG. 4 is a graph of the relative $K_i$ values of three commercial HIVPr inhibitor drugs, saquinavir, indinavir and ritonavir, and inhibitor UIC98-056 (using the $K_i$ of wild-type HIVPr as control value=1) against eleven HIVPr activities: wild-type, and ten HIVPr resistant mutants K20R, M461, L101, G48V, V82A, I64V, I93L, I15V, 184V, and L90M. The $K_i$ values of the wild-type HIVPr are shown in Table II. The relative $K_i$ values (in parenthesis of Table II and in FIG. 4) of the ten resistant mutants were calculated from the ratio of $K_i$ of the mutant HIVP/$K_i$ of the wild-type HIVPr. The key to the numbering of the mutants is shown in the inset of FIG. 4.

The synthesis of HIV protease inhibitor UIC-98-056 with hydroxyethylene and hydroxyethylamine isosteres is outlined in FIG. 3. The known lactone 1 was converted to acid 2 by lithium hydroxide mediated hydrolysis followed by protection of the alcohol functionality as tert-butyldimethylsilyl ether (Ghosh et al., 1998, *Synthesis*, 937 (Review); Ghosh et al., 1991, *J. Org. Chem.* 56:6500; Evens et al., 1985). The previously described (Ghosh et al., 1992, *J. Chem. Soc., Chem. Co.*, 273; Ghosh et al., 1998, *Synthesis*, 937 (Review)) azido epoxide 3 was reacted with isobutylamine in 2-propanol at 80° C. for 4 h and the resulting azidoalcohol was treated with m-tetrahydropyranyloxybenzenesulfonyl chloride 4 (Metanilic acid was diazotized at 0° C. and the resulting salt was boiled with water to obtain 3-hydroxybenzene sulfonic acid which was then treated with thionyl chloride/catalytic DMF/reflux to obtain sulfonyl chloride. The hydroxy group of the resulting 3-hydroxybenzene sulfonyl chloride was protected as THP ether by treating with DHP/catalytic PPTS in methylene chloride to get 4 as an oil.) in the presence of aqueous $NaHCO_3$ to provide the sulfonamide derivative 5. The azide functionality of 5 was hydrogenated over 10% Pd—C in methanol to afford the corresponding amine which was coupled with the acid 2 in the presence of 1-[3-dimethylaminopropyl]-3-ethylcarodiimide (EDC) and 1-hydroxybenzotriazole (HOBt) to afford the amide 6. Removal of the BOC group by treatment with aqueous hydrochloric acid and alkoxycarbonylation of the resulting amine with the known (Ghosh et al., 1993a) mixed active carbonate 7 in methylene chloride in the presence of 3 equivalents of triethylamine ($Et_3N$) 23° C. for 12 h afforded the inhibitor 8 (UIC-98-056).

EXPERIMENTAL (2S,4S,5R)-5-[N-(tert-Butoxycarbonyl)amino-4-tert-butyldimethylsilyloxy-2,5-dibenzyl pentanoic acid (2)

To a stirred suspension of lactone 1 (140 mg, 0.354 mmol) in a mixture (1:1) of DME and water (3 mL) at 0° C. was added LiOH monohydrate (29 mg, 0.71 mmol). After being stirred for 2 h, the reaction mixture was concentrated under reduced pressure. The aqueous layer was extracted with ethyl acetate (EtOAc) (2×10 mL). The combined organic layer was dried over anhydrous $Na_2SO_4$ and then concentrated under reduced pressure. The crude acid was dried under vacuum and dissolved in DMF (5 mL). Imidazole (956 mg, 6.4 mmol) was then added in portions followed by TBSCl (1.33 g, 12.7 mmol). The resulting reaction mixture was stirred at 23° C. for 48 h and then diluted with EtOAc (25 mL). The organic layer was washed with brine (3×20 mL) and dried over anhydrous $Na_2SO_4$. Evaporation of the solvent gave crude acid which was chromatographed (50% EtOAc/hexanes as the eluent) over silica gel to provide the title acid 2 (125 mg, 72%) as an oil: $^1H$ NMR exhibits a mixture of rotational isomers: $^1H$ NMR ($CDCl_3$, 400 Mhz): δ, 7.28–7.06 (m, 10H), 6.28 (m) and 4.72 (d, J=9.4 Hz) (for 1H), 4.11–3.64 (m, 2H), 2.99–2.46 (m, 5H), 1.88 (m) and 1.58 (m) (for 2H), 1.33 (s, 9H), 0.96 (s, 9H), 0.072–0.056 (m, 6H); IR (neat): 2952, 2928, 2858, 1711, 1658, 1406 $cm^{-1}$.

(2R,3S)-3-Azido-2-hydroxy-1-[[N-isobutylamino-N'-[(3-tetrahydropyranoxy)-benzenesulfonamido]yl]-4-phenylbutane (5)

To a stirred solution of 3 (546 mg, 2.9 mmol) in isopropanol (7 mL) was added isobtylamine (426 mg, 5.76 mmol) and the resulting reaction mixture was heated at 75° C. for 4 h. After this period, solvents were evaporated under reduced pressure and the resulting amine was dried under vacuum. To a stirred solution of this amine in $CH_2Cl_2$ (7 mL) was added sulfonyl chloride 4 (794 mg, 2.9 mmol) followed by aqueous $NaHCO_3$ solution (10%, 7 mL). The resulting mixture was stirred at 23° C. for 12 h. After this period, the organic layer was separated and then dried over anhydrous $Na_2SO_4$. Evaporation of the solvent under reduced pressure and chromatography of the residue over silica gel (25–30% EtOAc/hexanes) afforded the sulfonamide 5 (1.029 g, 85%) as an oil: $^1H$ NMR ($CDCl_3$, 200 Mhz): δ, 7.48–7.21 (m, 9H), 5.48 (m, 1H), 3.83–3.62 (m, 2H), 3.59–3.47 (m, 2H), 3.53 (dd, 1H, J=12.4, 3.3 Hz), 2.26 (dd, 1H, J=12.4, 8.8 Hz), 3.16–3.02 (m, 3H), 3.0–2.72 (m, 2H), 1.9–1.63 (m, 7H), 0.89 (dd, 6H, J=11, 6.6 Hz).

(2R,2'R,3S,4'S,5'S)-3-[N-[2'-Benzyl-5'-[(tert-butoxycarbonyl)amino]-4'-tert-butyldimethylsilyloxy-6'phenyl-1'-oxo]hexyl]amino-2-hydroxy-1-[N-isobutyl-amino-N'[3-tetrahydropyranoxybenzene)sulfonamido]]-4-phenylbutane (6)

To a stirred solution of the azide 5 (139 mg, 0.33 mmol) in methanol (3 mL) at 23° C. was suspended palladium on charcoal (10%, 15 mg). The resulting mixture was hydrogenated under a balloon filled hydrogen atmosphere for 12 h. After this period, the catalyst was filtered off through a pad of celite and the filter cake was washed with ethyl acetate (5 mL). Evaporation of the solvent furnished the amine obtained which was used for next reaction without further purification.

To a stirred solution of the acid 2 (120 mg, 0.24 mmol) in a mixture (1:3) of DMF and $CH_2Cl_2$ (3 mL) at 0° C. were added HOBt (32 mg 0.24 mmol) and EDC (46 mg, 0.24 mmol). The resulting mixture was stirred at 0° C. for 10 min. After this period, the above crude amine (156 mg, 0.4 mmol) in $CH_2Cl_2$ (0.5 ml) followed by diisopropylethylamine (51 mg, 0.4 mmol) were added. The resulting reaction mixture was stirred at 23° C. for 12 h. After this period, $CH_2Cl_2$ (15 mL) was added and the organic layer was washed with brine (2×10 mL) and then dried over anhydrous $Na_2SO_4$. Evaporation of the solvent under reduced pressure afforded a residue which was chromatographed (50% EtOAc/hexanes as the eluent) to obtain the amide 6 (221 mg, 68%) as an oil: $^1H$ NMR ($CDCl_3$, 400 MHz) δ, 7.43–6.9 (m, 19H), 5.82 (m, 1H), 5.48 (m, 1H), 4.73 (d, 1H, J=13.4 Hz), 3.93–3.82 (m, 3H), 3.65–3.51 (m, 2H), 3.15–2.21 (m, 13H), 1.90–1.63 (m, 9H), 1.38 (s, 9H), 0.93 (s, 9H), 0.78 (q, 6H, J=6.5 Hz), 0.02 (s, 3H), 0.011 (s, 3H).

(1'S,2R,2'R,3S,5'S)-3-[N-[2'-Benzyl-5'-[N-(2-tetrahydrofuranyloxycarbonyl]amino-4'-hydroxy-6'-phenyl-1'-oxo]hexyl]amino-2-hydroxy-1-[N-isobutylamino-N'[3-hydroxybenzene)sulfonamido]]-4-[phenylbutane (8)

To a stirred solution of the BOC derivative 6 (98 mg, 0.1 mmol) in a mixture (1:1) of EtOAc and water (2 mL) at 0° C. was added concentrated hydrochloric acid (0.2 mL). The resulting mixture was- stirred for 24 h and the reaction was concentrated under reduced pressure. The residue was dried under vacuum for 1 h and then dissolved in $CH_2Cl_2$ (2 mL). A solution of mixed carbonate 7 (29 mg, 0.1 mmol) in $CH_2Cl_2$ (1 mL) followed by $Et_3N$ (9.9 mg, 0.1 mmol) were added. The mixture was stirred for 12 h and then it was diluted with $CH_2Cl_2$ (15 mL) and washed with brine (10 mL). The organic layer was dried over anhydrous $Na_2SO_4$. Evaporation of the solvent under reduced pressure gave a residue which was chromatographed over silica gel (80% EtOAc/hexanes as the eluent) to fish the inhibitor 8 (35 mg, 45%): $^1H$ NMR ($CDCl_3$, 200 Mhz) δ, 7.64–7.03 (m, 19H), 5.64 (d, 1H, J=8.1 Hz), 5.29 (s, 2H), 5.1 (m, 1H), 4.74 (d, 1H, J=8.4 Hz), 4.22–3.58 (m, 8H), 3.04–2.32 (m, 8H), 2.15–1.62 (m, 8H), 0.9 (d, 6H, J=6.3 Hz).

EXAMPLE 2

Demonstration that Inhibitor UIC-99-056 Can Withstand Resistance

The inhibition constant, $K_i$, of UIC-98-056 was determined for the wild type HIV-1 protease and 10 mutants resistant to HIVPr inhibitors using the methods described by Ermolieff et al. (1997), *Biochemistry* 36:12364–12370. The wild-type HIV-1 Pr was produced as recombinant enzyme in *E. coli* as described by Ido et al. ( 1991) *J. Biol. Chem.* 266:24359–24366. The mutant enzymes were made by site-directed mutagenesis of the HIVPr gene either as described by Ermolieff et al., 1997, *Biochemistry* 36:12364–12370 or by a similar procedure. These mutants were identified in clinical trials and in vitro studies to resist saquinvair (mutants G48V and L90M, Jacobsen et al., 1996, *J. Infect. Diseases* 173:1379–1387), indinavir (mutants V82A, M46I and L10I, Condra et al., 1995; Lander, Richman and Vella (1998) HIV Resistance and Implications for Therapy MediCom.) and ritonavir (mutants L90M, V82A, K20R and M46I, Molla et al., 1996, *Nat. Med.* 2:760–765; Carder et al. (1998)). For direct comparison, the $K_i$ values against the wild-type HIVPr and ten mutants were also determined for saquinavir, indinavir and ritonavir.

Table II shows these $K_i$ values and the ratios (in parenthesis) between the inhibition constant of the mutants, $K_{i,mut}$, to the inhibition constant of the wild-type HIVPr taken as 1.0. The latter results are also plotted in FIG. 3. It can be seen clearly that for three commercial drugs, the $K_{i,mut}$ values of the resistant mutants are consistently higher than $K_i$ of the wild-type HIVPr (Table II and FIG. 3), indicating the resistance and cross-resistance properties of the mutants. In contrast, the same comparison for inhibitor UIC-98-056, the $K_{i,mut}$ values are nearly the same as $K_i$ value of the wild-type HIVPr for all mutants except mutant I84V, which increased 9-fold. Even in this mutant, the only significant increase observed is much less than the $K_i$ increase of the other three commercial inhibitors, which are 22-fold for ritonavir, 18-fold for indinavir and 13-fold for sequinavir (Table II and FIG. 3).

TABLE II $K_i$ values of the wild-type and resistant mutants of HIV-1 protease. Data are reported with standard errors and the fold of $K_i$ increase from that of the wild-type are shown in parenthesis.

| | $K_i$ (nM) | | | |
|---|---|---|---|---|
| | Saquinavir | Indinavir | Ritonavir | UIC-98-056 |
| W.T. | 0.20 ± 0.06 | 0.10 ± 0.02 | 0.20 ± 0.10 | 6.20 ± 0.80 |
| V82A | 1.53 ± 0.54(7.7) | 5.18 ± 0.55(51.8) | 2.40 ± 0.37(12.0) | 6.23 ± 1.20(1.0) |
| I84V | 2.62 ± 0.27(13.1) | 1.81 ± 0.03(18.1) | 4.49 ± 1.73(22.5) | 55.30 ± 0.46(8.9) |
| I15V | 0.38 ± 0.19(1.9) | 0.76 ± 0.13(7.6) | 0.78 ± 0.16(3.9) | 1.22 ± 0.14(0.2) |
| K20R | 0.81 ± 0.35(4.1) | 3.16 ± 0.61(31.6) | 1.99 ± 0.60(10.0) | 2.90 ± 0.74(0.5) |
| M46I | 3.36 ± 0.52(16.8) | 1.01 ± 0.49(10.1) | 14.73 ± 4.60(73.7) | 3.16 ± 0.81(0.5) |
| L10I | 1.74 ± 0.20(8.7) | 0.52 ± 0.23(5.2) | 1.50 ± 0.26(7.5) | 1.03 ± 0.25(0.2) |
| G48V | 2.70 ± 0.20(13.5) | 0.26 ± 0.02(2.6) | 0.10 ± 0.03(0.5) | 8.70 ± 1.40(1.4) |
| L90M | 0.60 ± 0.04(3.0) | 0.48 ± 0.06(4.8) | 0.51 ± 0.06(2.6) | 2.10 ± 0.50(0.3) |
| I64V | 0.94 ± 0.55(4.7) | 2.88 ± 0.60(28.8) | 2.50 ± 0.66(12.5) | 6.24 ± 1.52(1.0) |
| I93L | 6.82 ± 1.78(34.1) | 2.83 ± 0.76(28.3) | 1.20 ± 0.52(6.0) | 3.05 ± 0.64(0.5) |

These ten mutants are representative resistant mutants in the clinical trials for three commercial HIVPr inhibitor drugs. The results in Table II and FIG. 3 confirm the resistance by the observation of the $K_i$ increases from the wild-type to the mutant HIVPr against three commercial inhibitors. There are also considerable cross resistance of these mutants against all three commercial drugs (Table II and FIG. 3) as already well known in the literature (Rose et al., 1996, *Proc. Natl. Acad. Sci. USA* 93:1648–1653; Winslow and Otto, 1995, *AIDS* 9 (suppl A):S183-S192). Nine out of ten of the $K_i$ values of inhibitor UIC-98-056 did not change from the wild-type to mutant HIVPr's. The single $K_i$ increase for I84V is also less significant than that of the three commercial drugs. This property, which is unique and has not been previously accomplished, indicates that UCI-98-056 can withstand the development of HIVPr mutation-resistance.

We claim:

1. A polypeptide aspartic acid protease inhibitor having the following structure:

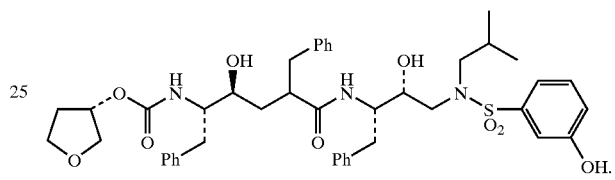

2. A method for treating a patient infected with a pathogen expression an aspartic acid protease comprising the oral administration of an aspartic acid protease inhibitor having the following structure:

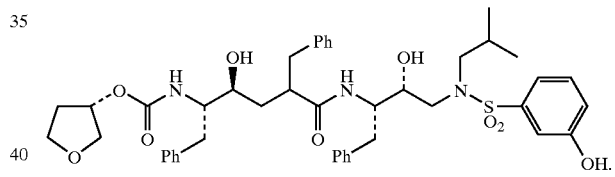

* * * * *

UNITED STATES PATENT AND TRADEMARK OFFICE
CERTIFICATE OF CORRECTION

PATENT NO. : 6,969,731 B1 Page 1 of 1
APPLICATION NO. : 09/506988
DATED : November 29, 2005
INVENTOR(S) : Tang et al.

It is certified that error appears in the above-identified patent and that said Letters Patent is hereby corrected as shown below:

In claim 2, column 12, line 31, delete "expression" and insert -- expressing -- therefor.

Signed and Sealed this

Twelfth Day of September, 2006

JON W. DUDAS
*Director of the United States Patent and Trademark Office*